(12) United States Patent
Vidal et al.

(10) Patent No.: US 8,746,882 B2
(45) Date of Patent: Jun. 10, 2014

(54) CUSTOMIZED INTRAOCULAR LENS POWER CALCULATION SYSTEM AND METHOD

(75) Inventors: Carmen Canovas Vidal, Groningen (NL); Pablo Artal, Murcia (ES); Marrie Van Der Mooren, Englebert (NL); Patricia Ann Piers, Groningen (NL)

(73) Assignee: Abbott Medical Optics Inc., Santa Ana, CA (US)

( * ) Notice: Subject to any disclaimer, the term of this patent is extended or adjusted under 35 U.S.C. 154(b) by 258 days.

(21) Appl. No.: 13/207,677

(22) Filed: Aug. 11, 2011

(65) Prior Publication Data

US 2012/0044454 A1 Feb. 23, 2012

Related U.S. Application Data

(60) Provisional application No. 61/418,319, filed on Nov. 30, 2010, provisional application No. 61/374,657, filed on Aug. 18, 2010.

(51) Int. Cl.
*A61B 3/10* (2006.01)
*A61B 3/103* (2006.01)
*A61F 2/16* (2006.01)

(52) U.S. Cl.
CPC .. *A61B 3/103* (2013.01); *A61F 2/16* (2013.01)
USPC .......................................... 351/205; 351/246

(58) Field of Classification Search
CPC ................................. A61B 3/103; A61F 2/16
USPC .................. 351/205, 246; 623/6.11
See application file for complete search history.

(56) References Cited

U.S. PATENT DOCUMENTS 8,211,172 B2 * 7/2012 Hong et al. .................. 623/6.11
2012/0310337 A1* 12/2012 Hacker et al. ................ 623/6.11

OTHER PUBLICATIONS

Abenza S., et al., "Advanced Methods for the Calculation of Intraocular Lens Power," Murica, Apr. 3, 2008.
Canovas C., et al., "Customized Eye Models for Determining Optimized Intraocular Lenses Power," Biomedical Optics Express, 2011, vol. 2 (6), pp. 1649-1662.
Canovas C., et al., "Customized Ray-tracing Modelling for Optimized IOL Power Calculations," XXVI Congress of ESCRS, 2008.
Canovas C., et al., "Optimized IOL Power Predicted by Customized Modelling," Association for Research in Vision and Ophthalmoloy, 2007.
Canovas C., et al., "Optimized IOL Power Predicted by Customized Modelling," Investigative Ophthalmology and Visual Science, 2007, vol. 48, E-Abstract 1092.
Canovas C., et al., "Optimized IOL Power Predicted by Customized Modelling," Presentation University, 2008.

(Continued)

*Primary Examiner* — Huy K Mai
(74) *Attorney, Agent, or Firm* — Abbott Medical Optics Inc.

(57) ABSTRACT

Selecting an optimal intraocular lens (IOL) from a plurality of IOLs for implanting in a subject eye, including measuring anterior corneal topography (ACT), axial length (AXL), and anterior chamber depth (ACD) of a subject eye; selecting a default equivalent refractive index depending on preoperative patient's stage or calculating a personalized value or introducing a complete topographic representation if posterior corneal data are available; creating a customized model of the subject eye with each of a plurality of identified intraocular lenses (IOL) implanted, performing a ray tracing through that model eye; calculating from the ray tracing a RpMTF or RMTF value; and selecting the IOL corresponding to the highest RpMTF or RMTF value for implanting in the subject eye.

21 Claims, 10 Drawing Sheets

(56) References Cited

OTHER PUBLICATIONS

Canovas C., et al., "Practical Demonstrations on Ray-tracing for Eye Model Design," Laboratory of Optics, 2010.

Canovas C., et al., "Ray-Tracing Prediction of Intraocular Lenses Power: Effect of Corneal Aberations," Association for Research in Vision and Ophthalmology, 2009.

Canovas C., et al., "Ray-Tracing Prediction of Intraocular Lenses Power: Effect of Corneal Aberrations," Investigative Ophthalmology and Visual Science, 2009, vol. 50, E-Abstract 1157.

Co-pending U.S. Appl. No. 61/480,589.

Dubbelman M., et al., "The Shape of the Aging Human Lens: Curvature, Equivalent Refractive Index and the Lens Paradox," Vision Research, 2001, vol. 41 (14), pp. 1867-1877.

Perez-Escudero A., et al., "Minor Influence of Myopic Laser in Situ Keratomileusis on the Posterior Corneal Surface," Investigative Ophthalmology and Visual Science, 2009, vol. 50 (9), pp. 4146-4154.

Canovas C., et al., "Customized Ray-Tracing Modelling for Optimized IOL Power Calculations," IOL Technology, 1647; 2008.

* cited by examiner

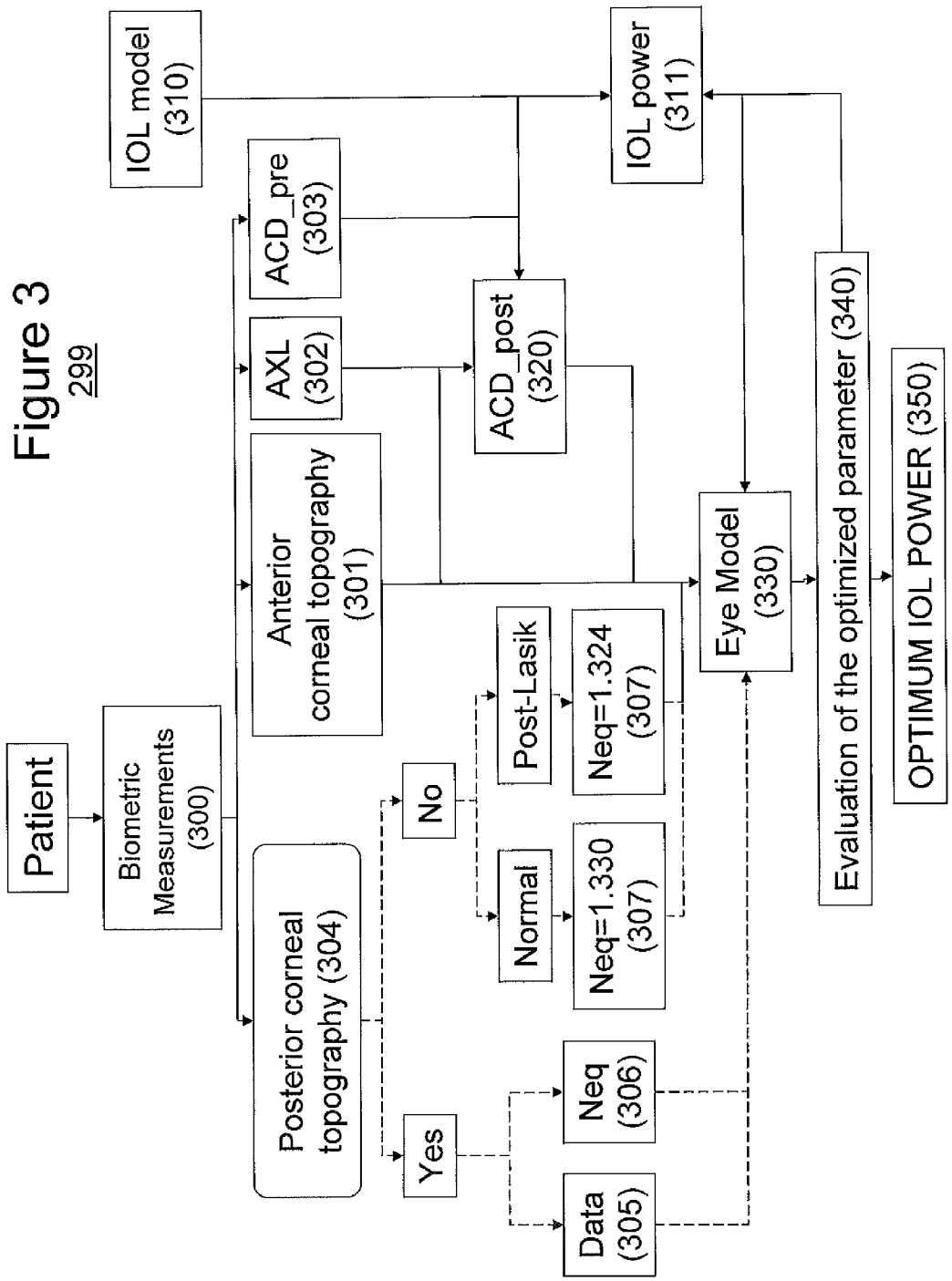

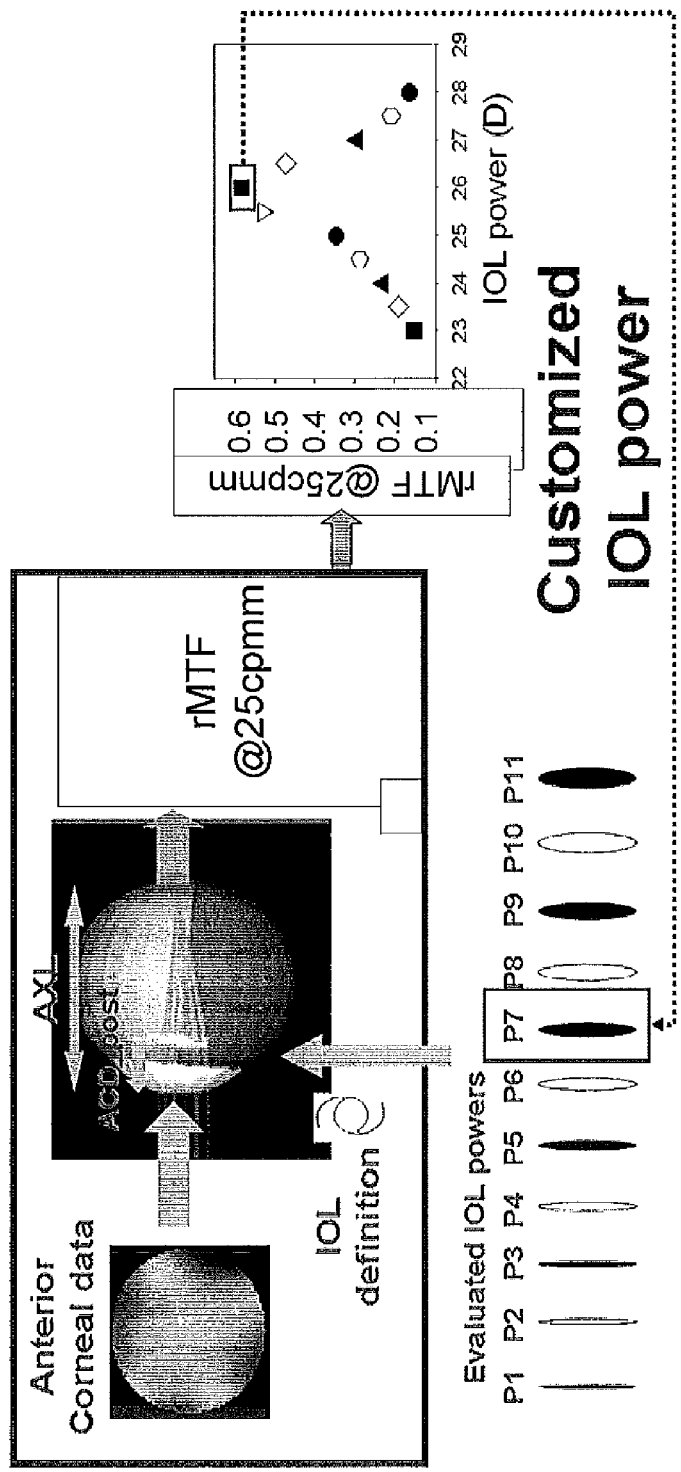

CUSTOMIZED INTRAOCULAR LENS POWER CALCULATION SYSTEM AND METHOD

CROSS-REFERENCE TO RELATED APPLICATIONS

This application claims priority to U.S. Patent Application Ser. No. 61/418,319, under the same title, filed Nov. 30, 2010, and also claims priority to U.S. Patent Application Ser. No. 61/374,657, entitled "An Apparatus, System and Method for an Empirically-Based, Customized Intraocular Lens Power Calculation," filed Aug. 20, 2010, the entire contents of both of which are incorporated herein by reference as if set forth herein in the entirety. Full Paris Convention priority is hereby expressly reserved.

BACKGROUND OF THE INVENTION

1. Field of the Invention

The present invention relates generally to power calculations for intraocular lenses (IOLs) and more particularly, is directed to a customized polychromatic or monochromatic ray tracing-based IOL power calculation that includes subject eye measurement data, resulting in an improved IOL power calculation compared to prior regression-based IOL power calculations, particularly for patients that previously underwent an ablative form of keratorefractive surgery, such as lasik.

2. Description of the Background

Intraocular Lenses (IOLs) may be used for restoring visual performance after removal of the natural crystalline lens of an eye, such as in cataract surgery. Because the IOL geometry may be selected, it is desirable to select an IOL geometry that will most nearly achieve emmetropia when the IOL is implanted. The term emmetropia, and variations thereof, is used herein and within the art to indicate a state of vision in which an object at effectively infinite distance from the subject is in sharp focus on the subject's retina.

The power necessary for the IOL to provide emmetropia has typically been calculated using classical regression theory. For example, the Saunders, Retzlaff, and Kraff formula (SRK) is a regression formula derived from clinical data to indicate the optimal power for an IOL. The SRK regression formula is:

$$P = A - 2.5*AXL - 0.9*K$$

where P is the IOL power, A is the lens constant, AXL is the axial length in millimeters of the subject eye, and K is the average corneal power in diopters (D). Because the SRK regression formula was derived from historical clinical data, it necessarily provides the best result when the subject eye has dimensions similar to the most common eye dimensions that were included in the clinical data from which the formula was derived. In particular, the SRK typically underestimates the necessary IOL power to obtain emmetropia for short eyes, and overestimates the IOL power necessary for long eyes. That is, use of the SRK formula may lead to the selection of an IOL power for long eyes that is too strong, and an IOL power for short eyes that is too weak.

In order to remedy these shortcomings of SRK, other regression formulas were developed that incorporate certain refinements, but which are still based on the analysis of historical clinical data. In the SRK II regression for example, an additional constant F is included to adjust the IOL power calculation based on the length of the eye. More particularly, the SRK II formula is:

$$P = A - 2.5*AXL - 0.9*K + F$$

wherein F is a known value, which may be equal to +3 D at less than 20 millimeters of axial length (AXL), +2 D at 20 to 20.9 millimeters, +1 D at 21 to 21.9 millimeters, 0D at 22 to 22.5 millimeters, and −0.5 D at greater than 24.5 millimeters. By way of example, if SRK yields an IOL power of +32 D, SRK II may yield an IOL power of +35 D (+32 D+3 D=+35 D) if the patient's AXL is less than 20 mm.

An additional regression method, developed in an effort to address the shortcomings of SRK and SRK II, is the SRK/T method. In the SRK/T, the approach is different. An empirical regression method is used for prediction of the IOL position after the surgery. Once that position is determined, the preferred power for an IOL to be implanted is calculated by simple paraxial optics, taking into account that the eye can be modeled under this approximation as a two lens system (cornea+IOL) focusing an image on the retina. This approach is based on Fyodorov's theoretical formula.

Thus, there currently exists a large catalog of formulas for calculating IOL power, such as the aforementioned SRK/T, as well as, Haigis, Hoffer Q, and Holladay 1 and 2, for example. It is well known that these formulas do not provide accurate predictions for all preoperative refractive states. While a good prediction to achieve emmetropia after surgery may be obtained for patients that were emmetropes or close to emmetropia prior to cataract surgery, errors arise for extreme myopes or hyperopes. Such deviations for "non-normal" eyes are not unexpected, since the regression formulas were derived from analyses of historical data, and therefore necessarily make recommendations that are most favorable for "normal eyes."

For example, FIG. 1 illustrates the variations in IOL power recommendations provided by different regression calculation methods for a set of patients, each indicated by a patient number. As illustrated, the differences in IOL power recommended by the various methods for a particular patient are small when the patient has "normal eyes," indicated by the shaded rectangular area 100. However, the differences become more extreme for progressively more myopic or hyperopic eyes, particularly for eyes having a recommended IOL power less than about 17 D and greater than about 24 D.

Optical aberrations are another important point that is not taken into account in regular regression formulas. There are two main types of aberrations, monochromatic and polychromatic. The former may be related with either the cornea or the IOL, while the latter is mainly related to the IOL material. Every specific eye has a different pattern of monochromatic aberrations and therefore their impact cannot be averaged by optimized constants or regression coefficients. In addition, due to the paraxial nature of regular regression formulas, the impact of optical aberrations is totally neglected.

Eyes that have undergone refractive surgery, such as radial keratotomy (RK), photorefractive keratectomy (PRK), laser-assisted in situ keratomileusis (lasik), or the like, are another example of eyes that are out of the "normal" range, at least in part because the corneal power of the post operative eye has been modified by the refractive surgery. Thus, it is well known that regression formulas typically do not provide proper IOL power for those patients. Other factors that complicate predicting an optimal IOL power for such patients include the corneal power (K), which may be incorrectly measured by topographers or keratometers after a refractive surgery procedure. In addition, the expected relationship between the anterior and posterior corneal radius may be modified by refractive surgery, which renders the corneal equivalent refractive index calculated for normal patients inapplicable, leading to an inaccurate total corneal power.

Moreover, it has been widely reported that standard ablative forms of keratorefractive surgery, such as lasik, may result in a larger than normal proportion of corneal aberrations. Such aberrations may affect the IOL power predicted by the regression formulas, which do not consider such aberrations, due to their paraxial nature.

Thus, there is a need for a system and method that provides improved accuracy in predicting optimal IOL power for patients whose eyes are inside as well as outside of the normal range, with respect to axial lengths, amount of aberrations or preoperative state.

SUMMARY OF THE INVENTION

The present invention is and includes a system and a method of selecting an intraocular lens (IOL) to be implanted in a subject eye. The system and method may include measuring anterior and if possible, posterior corneal topography, an axial length (AXL), and an anterior chamber depth (ACD) of a subject eye, and for each of a plurality of intraocular lenses (IOLs), simulating the subject eye with the intraocular lens (IOL) implanted in accordance with the measuring, performing either monochromatic or polychromatic ray tracing through the surfaces defining the built eye model, calculating from the ray tracing a modulation transfer function (MTF)-based value, and selecting the IOL corresponding to a highest one of the MTF value for implanting in the subject eye.

The calculating of the ray tracing may be performed polychromatically or monochromatically, depending on the IOL material, at a suitable entrance pupil, such as at or at about a 4 mm entrance pupil, for example. Further, the polychromatic ray tracing may be performed at about six (6) wavelengths weighted according the spectral sensitivity curve in photonic or mesopic conditions, although other suitable numbers of wavelengths may be used according to the present invention.

The calculating of the radially averaged polychromatic modulation transfer function (RpMTF) (or its monochromatic version (RMTF) if a monochromatic ray tracing is performed) value may be with regard to a single optical resolution, herein referred to as "point values," such as with respect to calculation of the RpMTF/RMTF at or at about 25 cpmm. Alternatively, the calculating from the ray tracing of the RpMTF/RMTF value may comprise calculating the area under a RpMTF/RMTF curve, wherein each curve pertains to the RpMTF/RMTF at a plurality of optical resolutions. Those skilled in the art will recognize that MTF Volume, Visual Strehl ratio or other suitable optical metrics for predicting the optical quality for each individual IOL model in the customized eye model may be used.

The system and method may further be, with respect to a first measuring device, capable of providing a plurality of characteristics of a subject eye, and, when associated with a computing device programmed with at least one characteristic for each of a plurality of identified IOLs, may further predict a position of the identified IOL when implanted in the subject eye, simulate the subject eye based on the plurality of characteristics, perform a ray tracing based on the customized eye model, calculate from the ray tracing a point from the RpMTF/RMTF value, and compare a plurality of RpMTF/RMTF values corresponding to the plurality of considered IOLs to identify a highest one of RpMTF/RMTF values. Further, the devices may be employed to identify one IOL from the plurality of IOLs corresponding to the highest one of RpMTF/RMTF values, and may output the identified one of the IOLs. The system and method of the present invention may be embodied in a tangible computer-readable storage device storing computer instructions which, when read by a computer, cause the computer to perform the steps discussed herein.

Therefore, the present invention provides a system and method that provides improved accuracy in predicting optimal IOL power for patients whose eyes are inside as well as outside of the normal range.

BRIEF DESCRIPTION OF THE DRAWINGS

The accompanying drawings are included to provide a further understanding of the herein described systems and methods, and to illustrate certain embodiments and aspects thereof. Together with the description they are intended to explain, but unless expressly stated not to limit, the principles of the herein disclosed systems and methods.

In the drawings, like numerals represent like parts, and:

FIG. 3 is a flow diagram illustrating the method steps for selecting an optimal IOL from a plurality of known IOLs for implanting in a subject eye, in accordance with the herein disclosed systems and methods;

FIGS. 4A and 4B illustrate exemplary methods of selecting an optimal IOL from a plurality of known IOLs for implanting in a subject eye;

DETAILED DESCRIPTION

It is to be understood that the herein disclosed systems and methods may have been simplified to illustrate elements that are relevant for a clear understanding of the present invention as defined by the appended claims, while eliminating, for the purpose of clarity, many other elements and/or steps found in typical intraocular lens systems and methods. Those of ordinary skill in the art may thus recognize that additional elements and/or steps may be desirable and/or required to implement the herein described systems and methods. However, because such elements and steps are well known in the art, and because they do not facilitate a better understanding of the present invention, a discussion of such elements and steps is not provided herein. The present disclosure is intended to include all such elements and steps known to those of ordinary skill in the art.

The herein disclosed systems and methods provide a unique and customizable procedure for calculating a recommended power of a particular IOL to be implanted in the eye of a particular individual. The systems and methods are applicable to patients having either normal or non-normal eyes, including all levels of corneal aberrations. An increased level of such aberrations may commonly be found in patients who previously underwent an ablative form of keratorefractive surgery for correcting different ametropias, such as photorefractive keratectomy (PRK), laser-assisted in situ keratomileusis (lasik), and the like, although patients presenting corneal aberrations arising from other causes may also benefit from the herein described systems and methods. The system and methods herein disclosed include, if needed, both monochromatic and polychromatic aberrations of the IOL model to implant. Therefore, the system provides a model for predicting optical quality of the patient's eye with the implanted IOL.

The herein described systems and methods provide the unique and customizable, optimized outcome for a particular patient in accordance with the unique characteristics of the subject patient's eye, and in conjunction with a series of lens models that may be simulated in the model of the subject patient's eye. The selected lens may satisfy maximization criteria, such as the area under a modulation transfer function curve, or may be less processing intensive when optimized based on a point value, herein defined to be the value of a modulation transfer function at a single resolution, such as the radially averaged polychromatic or monochromatic modulation transfer function value at 25 cpmm, for example. Some other metrics for prediction of optical quality may also be considered.

Figure 1:
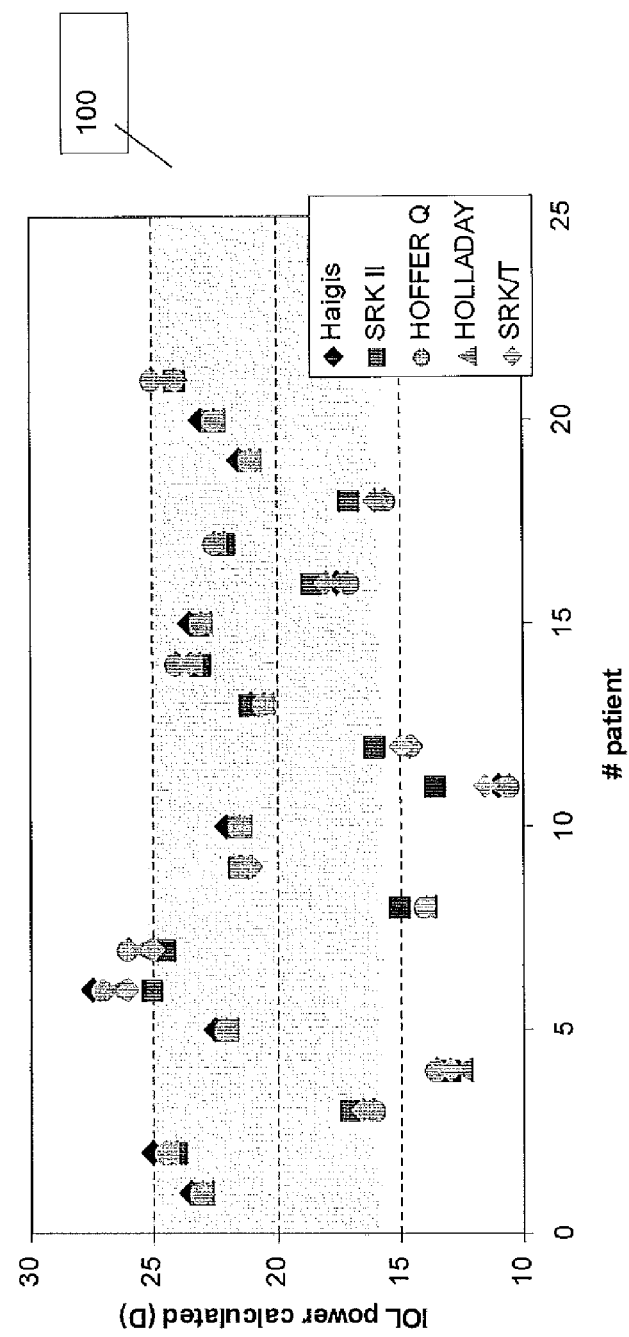
FIG. 1 illustrates the variations in IOL power recommendations provided by different regression calculation methods in a large range of patients covering different axial lengths.
Figure 2:
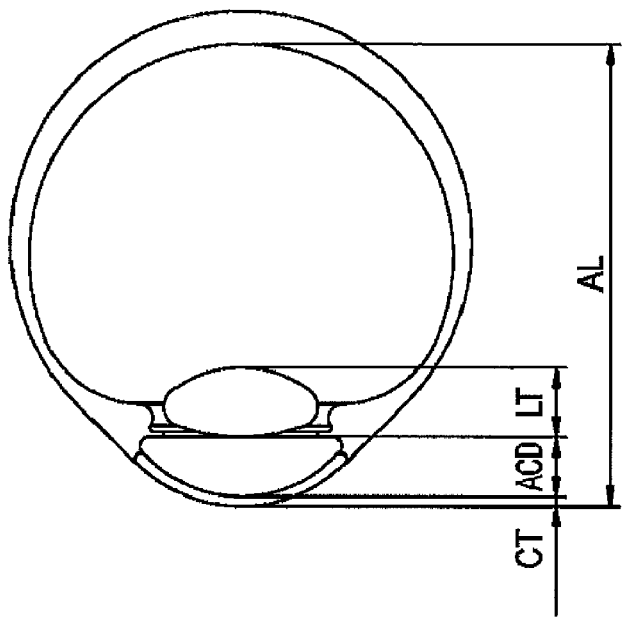
FIG. 2 is an illustration of a human eye showing dimensions useful in the herein described systems and methods.

FIG. 2 is a schematic drawing of a human eye 200. Light enters the eye from the left of FIG. 2, and refracts into the cornea 210, passes through the anterior chamber 220, the iris 230 through the pupil, and reaches lens 240. After refracting into the lens, light passes through the vitreous chamber 250, and strikes the retina 260, which detects the light and converts it to an electric signal transmitted through the optic nerve to the brain (not shown). As indicated, cornea 210 has corneal thickness (CT), here considered as the distance between the anterior and posterior surfaces of the cornea. Anterior chamber 220 has anterior chamber depth (ACD), which is the distance between the anterior surface of the cornea and the anterior surface of the lens. Lens 230 has lens thickness (LT) which is the distance between the anterior and posterior surfaces of the lens. The eye has an axial length (AXL) which is the distance between the anterior surface of the cornea and the retina, where the image should focus.

The anterior chamber 220 is filled with aqueous humor, and optically communicates through the lens with the vitreous chamber, which occupies the posterior ⅘ or so of the eyeball and is filled with vitreous humor. The average adult eye has an ACD of about 3.15 mm, with a large variability between individuals.

A customized eye model may be built when parameters defining that specific eye are measured and introduced. Such parameters may include, for example, anterior corneal elevations from where anterior corneal wavefront aberrations can be calculated. Anterior corneal elevations may be assessed, for example, using a placido based topographer, such as a Humphrey® ATLAS Corneal Topography System available from Carl Zeiss Meditec, Inc. or the like. The dimensions of the subject eye, including the ACD and AXL, may also be assessed, for example, using a Zeiss IOLMaster®. Finally, refractive indexes corresponding to the different optical surfaces considered in the eye model can be custom modeled or introduced as parameters from prior models.

The herein disclosed systems and methods are directed to selecting characteristics, such as optical power, particularly for spherical and aspherical intraocular lenses (IOLs), such as to provide an optimal refractive outcome for patients having either "normal" or "non-normal" eye dimensions. An IOL comprises an optic, or clear portion, for focusing light, and may also include one or more haptics that are attached to the optic and may serve to center the optic under the pupil, for example, by coupling the optic to zonular fibers of the eye. In various embodiments, a modeled eye with an IOL implanted may also include other information of the IOL, such as the location of IOL within eye as indicated, for example, by the post-implant ACD. Some other predictive aspects may be introduced, such as an average tilt and decentration corresponding to the particular IOL model, surgeon and surgical technique.

The optic of the IOL has an anterior surface and a posterior surface, each having a particular shape that contributes to the refractive properties of the lens. Either or both of these lens surfaces may optionally have a diffractive element made integral with, or attached to, the surfaces. The refractive and/or diffractive elements on the anterior and/or posterior surfaces may also have anamorphic or toric features that can generate astigmatism to offset the astigmatism from the cornea of a particular subject eye.

Once the anterior cornea is assessed and the eye dimensions determined, the herein disclosed systems and methods may be used to select an IOL to provide, as nearly as possible, emmetropic vision. For example, an IOL may be selected from a range of lenses having known properties available from one or more IOL manufactures, each lens having its own distinct optical properties, such as power. The available power values may be in increments of or about 0.5 diopters, or any suitable value.

One measurement of the quality of the system composed by the eye and the implanted IOL power is the modulation transfer function (MTF). This function shows how an optical system transfers the frequency content from the object to the image. The higher the MTF value, the better the optical system. This function is closely related to contrast sensitivity measurements, and is also related to visual acuity when maximum contrast is considered. A human eye with excellent acuity can resolve about 30 sinusoidal cycles of black and white areas per degree, expressed in cycles per degree (cpd). Alternatively, MTF may be related to spatial frequency in terms of sinusoidal cycles of black and white areas distinguishable per millimeter, expressed as cycles per millimeter (cpmm), for example, 25, 50, or 100 cpmm. Spatial frequencies like 25 cpmm are especially interesting in vision, because the peak of contrast sensitivity related to the visual system is in this region.

The herein disclosed systems and methods provide a customizable procedure for predicting the optimum IOL characteristics of a specific IOL for a particular eye of a patient. The systems and methods discussed herein, and more particularly as discussed with respect to FIGS. 3, 4A and B, and 7, in formulating the recommendation of IOL characteristics, may thus preferably take into account the unique biometric parameters of the subject eye, such as the AXL and the ACD as well as anterior corneal aberrations of the subject eye.

FIG. 3 is a flow diagram illustrating the steps of a customized IOL power prediction method 299. A determination may be made of the eye's pre-operative parameters at step 300. In particular, the eye's anterior corneal topography (ACTP) parameters may be assessed, including, for example, the eye's corneal elevations, corneal wavefront aberrations and the like, such as using a topographer device such as a Humphrey® Atlas™ Corneal Topography System available from Carl Zeiss Meditec, Inc. (Step 301). In addition, the eye's AXL and ACD may also be determined, for example, using an IOLMaster, also available from Carl Zeiss Meditec, Inc. (Steps 302 and 303 respectively).

The ACTP, AXL, ACD may be input into a computer program at step 330, as well as the geometries corresponding to different IOL models and/or powers to evaluate described hereinafter. These customized inputs suffice for the computer program to run, although other inputs may be introduced as described hereinafter. The computer program comprises computer readable instructions that may be stored in a tangible computer readable storage medium, such as a hard drive, optical disk, volatile or non-volatile memory, or the like. The program instructions, when read and executed by a computer, such as on one or more microprocessors, cause the computer to perform work. Here, a computer user, such as an ophthalmologist, may input the ACTP, AXL and ACD into the program, such as using input devices such as a keyboard and mouse in combination with a user interface, such as a graphical or text-based user interface. The computer may manipulate the data in accordance with the program instructions and provide an output for viewing by the user, such as on a video monitor, or by printing on a printer.

The final post-implantation position of the IOL may be calculated at step 320 from the biometric data entered into the computer program. The position may be predicted from the measured AXL and pre-operative ACD at steps 302 and 303 respectively, using a regression formula based on historical clinical data relating a plurality of pre-operative ACDs (ACD_pre) and AXLs with the corresponding post-operative ACD (ACD_post).

In general, different regression formulas may be obtained or used for different IOL models, as will be understood to those skilled in the art. As used herein, an "IOL model" is used to refer to a modeling of a series of IOLs each having different power, typically from the same manufacturer and having known geometries and/or parameters. The post-operative position of the IOLs of a particular IOL model may be described by a regression correlation that is developed for that particular IOL model from the biometric data previously described, and may be used to predict the post-operative position of any of the IOL powers for that IOL model. Exemplary regression formulas are those presented by Norrby et al at ARVO 2010 Annual Meeting:

$$ACD\_post = 1.711 + 0.092*AXL + 0.314*ACD\_pre \text{ (for the ZCB00)}$$

$$ACD\_post = 1.048 + 0.100*AXL + 0.351*ACD\_pre \text{ (for the ZA9003)}$$

although other formulas may be used to predict the IOL placement at step 320, as presented recently by the authors [Canovas C and Artal P, "Customized eye models for determining optimized intraocular lenses power," Biomed. Opt. Express 2011; 2: 1649-1662]. Another possible embodiment might be related to the use of the idea contained in U.S. patent application No. 61/480,589 entitled "Systems and Methods for Determining IOL Lens Power", filed on Apr. 29, 2011, the entire contents of which are incorporated herein by reference.

The computer program may use as input characteristics of the IOL modeling at step 330, a prediction of a typical or proper post-operative IOL placement for that IOL model using an appropriate regression formula for that IOL model. Regression formulas for various IOL models may be incorporated into the program by its publisher, for example, or may be added to the program by a user at any convenient time using a module provided by the computer program and/or IOL provider for that purpose.

More particularly, the computer program into which the eye parameters are input at step 300 may provide for different approaches to modeling the eye at step 330, depending on the measured information that is available. All approaches may incorporate the patient's anterior corneal topography (ACT), ACD, and AXL, as described hereinbefore, being the IOL placement predicted as has been hereinbefore described. Also in order to include the refraction relating to the posterior corneal surface in the model, parameters defining a patient's posterior cornea may be directly introduced in the model as an input at step 305, or by means of a customized equivalent refractive index at optional step 306, or a default equivalent refractive index related to the patient's preoperative stage may be introduced at optional step 307 to account in step 330 for the refraction or some other optical properties of the posterior cornea. This equivalent refractive index is an artificial index considered from the anterior cornea to the anterior IOL surface, in order to achieve the same power as the total cornea while only considering the anterior surface.

If there is no measurement data available pertaining to the posterior cornea and corneal thickness of a subject eye, then an average equivalent refractive index from the anterior cornea to the anterior IOL surface may be defined at step 307 to be 1.330 for a "normal" eye, meaning that the eye had not undergone previous lasik surgery or the like. However, if the eye had undergone myopic lasik surgery or the like, an average equivalent refractive index of about 1.324 may be used. For eyes that have undergone standard LASIK procedures for hyperopia correction, an equivalent refractive index may be further determined for a significant sample of eyes according to the method described herein below. Those skilled in the art will appreciate that the equivalent refractive indexes either for normal or myopic post-LASIK patients herein disclosed may be further optimized according to the same procedure.

If measurement data is available pertaining to the posterior cornea radius (r2), defined as an average radius or as corresponding to at least two meridians or even a complete representation of the posterior corneal by means of a set of elevations similar to the description used for the anterior cornea, and the corneal thickness (ct), such as may be obtained, for example, using an instrument as a scheimpflug camera, then these values may be input into the computer program of method 299. These values may be considered as a directed input for the eye model. Therefore, the cornea is referred to as a two surface system, where the anterior cornea is related to anterior corneal topography measurements, and the posterior cornea is defined by those parameters measured for this corneal surface, including radius, and eventually aspheric terms and/or posterior corneal elevations. Both corneal surfaces may be separated by a distance equivalent to the corneal thickness measured for the subject.

In an alternative embodiment, if patient's measurement data are available pertaining to the posterior cornea radius (r2), and the corneal thickness (ct), such as may be obtained, for example, using an instrument as a scheimpflug camera, those values may be input into the computer program of method 299. The program can then determine a customized equivalent refractive index at step 306 using the following procedure:

1. Corneal power (Pmeasured) can be obtained directly from a topographer or keratometer or may be calculated from the anterior corneal topography by means of ray tracing performed at 4 mm pupil. The focal of the cornea (fcorn) is calculated as that minimizes the image spot size. From that, corneal power (Pmeasured) can be calculated as:

$$P\text{measured} = n/(f\text{corn})$$

where n is the keratometric index used by the corneal topographer or keratometer used for assessing the anterior cornea. Typical values include 1.3375, 1.332 or 1.3315.

2. Calculate a true anterior corneal radius as:

$r1 = (n-1)/P\text{measured}$;

3. Calculate true anterior corneal power (P1) as:

$P1 = (1.376-1)/r1$;

4. Calculate posterior corneal power (P2) as:

$P2 = (1.336-1.376)/r2$;

5. Calculate total corneal power (P) considering both corneal surfaces as:

$P = P1 + P2 - (ct/1.376)*P1*P2$; and

6. Calculate the equivalent refractive index as:

$n\text{eff} = (r1*P) + 1$.

It is important to note that all the distances are referred to be in meters and powers in diopters.

In order to stress the validity of the average equivalent refractive index for normals when posterior corneal data are not available, data from different eye models and also data found in the literature have been used to compare the different equivalent refractive index for normals. The parameters based on certain select models are shown in Table 1 for normal eyes, i.e., eyes that have not undergone myopic Lasik surgery, or the like.

TABLE 1

| Eye model | Ra | Rp | Rp/Ra | corneal thickness | neff |
|---|---|---|---|---|---|
| Le grand | 7.8 | 6.5 | 0.833333 | 500 | 1.33038 |
| Gullstrand | 7.7 | 6.8 | 0.883117 | 500 | 1.3315 |
| Dubbelman [1] | 7.79 | 6.53 | 0.838254 | 579 | 1.329251 |

Ra is referred to be the anterior corneal radius and Rp the posterior, all in millimeters. Neff is the equivalent refractive index. The last set of parameters refer to a bibliographic reference that can be found as [1] Dubbelman M, Sicam V A, Van der Heijde G L, "The shape of the anterior and posterior surface of the aging human cornea", Vision Res. 2006; 46: 993-1001.

In all the cases, the equivalent refractive index is on average similar to that consider as average for normals.

In contrast, the results of these parameters based on values found in the literature for a set of eyes both before and after standard myopic LASIK surgery, are shown in Table 2.

TABLE 2

| Perez-Escudero [2] | Ra | Rp | Rp/Ra | corneal thickness | Neff |
|---|---|---|---|---|---|
| Postlasik_pre | 7.70 | 6.38 | 0.83 | 572 | 1.329 |
| Postlasik_post | 8.52 | 6.37 | 0.75 | 493 | 1.323 |

Where [2] makes reference to the paper Perez-Escudero A, Dorronsoro C, Sawides L, Remon L, Merayo-Lloves J and Marcos S, "Minor Influence of Myopic Laser In Situ Keratomileusis on the Posterior Corneal Surface", Invest Ophthalmol Vis Sci. 2009; 50:4146-4154

In particular, the above tables illustrate the change in equivalent refractive index (neff) when an eye undergoes lasik surgery. The average corrected refraction by the Lasik surgery was −4 D. As shown, the reduced CT and changed anterior cornea of the post-lasik eye results in a neff lower than in the normal state. Accordingly, a downward adjustment of the equivalent refractive index from that used for normal eyes has been incorporated for postlasik eyes in the herein disclosed systems and methods, when posterior corneal data are not measured.

The geometry and optical properties of a select group of IOLs may also be obtained, for example, from a manufacturer, and may be resident in the program at step 311. Using the information of steps 300 in general, containing all the biometric measurements available and having selected the method to consider the refraction related to posterior cornea, 311, 320, the program at step 330 may effectively build a separate eye model (i.e., a mathematical description of the eye including an implanted IOL) defined by the biometric parameters at step 300, the IOL position predicted at step 310 for each of the IOL powers at step 311, and subject the eye model to either a monochromatic or polychromatic exact ray tracing (further described hereinafter) at this step 330 at or about at, for example, 4 mm pupil and white light at six (6) wavelengths if a polychromatic procedure is performed or at 540 nm for monochromatic considerations, although, as would be understood by those skilled in the art, other light sources, pupil diameters, and wavelengths may be used. The ray tracing may allow for calculation of various optical quality parameters, such as the point spread function (PSF) of the eye with the IOLs of the IOL model, from which one or more RpMTF/RMTF values can be obtained.

In a particular exemplary embodiment, based on the ray tracing, the program may calculate a RpMTF/RMTF point value for the eye, with each of the IOLs, at step 340. This calculation of RpMTF/RMTF at step 340 may preferably be at 25 cpmm or 50 cpmm, for example, although other spatial frequencies may be used to calculate one or more RpMTF/RMTF values for each of the IOLs. The IOL selected for implantation at step 350 is that which results in the highest calculated RpMTF/RMTF value. Alternatively, RpMTF/RMTF values for a range of frequencies may be calculated and used to define an RpMTF/RMTF curve for each IOL, the area under each curve may then be calculated for each IOL power evaluated in the eye model, and the greatest area may be used to select the IOL, as is described further hereinbelow. However, as appreciated by those skilled in the art, other optical metrics may be used for evaluating the optical quality of the customized eye model with a particular IOL model selected, following the same maximization process as herein before described.

The ray tracing procedure for assessing optimum IOL power in the present invention takes into account parameters of a particular IOL, as well as measurements pertaining to parameters of a particular eye. This procedure might be performed either in monochromatic or polychromatic conditions. More particularly, as used herein, a polychromatic ray tracing is one that employs multiple wavelengths of light so that chromatic aberration may also be accounted for and a ray tracing procedure is a procedure that simulates light propagation and refraction through an optical system by means of an exact solution of Snell's law, for light rays passing through the system. Illustratively, an entrance pupil of 4 mm may be selected, as referenced above, at least in part because a 4 mm pupil is realistic for cataract patients, and is large enough to allow for the introduction of monochromatic eye aberrations, which are omitted in paraxial optics (herein defined as the optics related to small angles and close proximity to the optical axis, which is analogous to using a small aperture, i.e. a small pupil). As such, the subject eye may be modeled through ray tracing of the path of multiple wavelength light passing through the modeled eye at a 4 mm pupil, although other pupil sizes may alternatively be selected.

Figure 9:
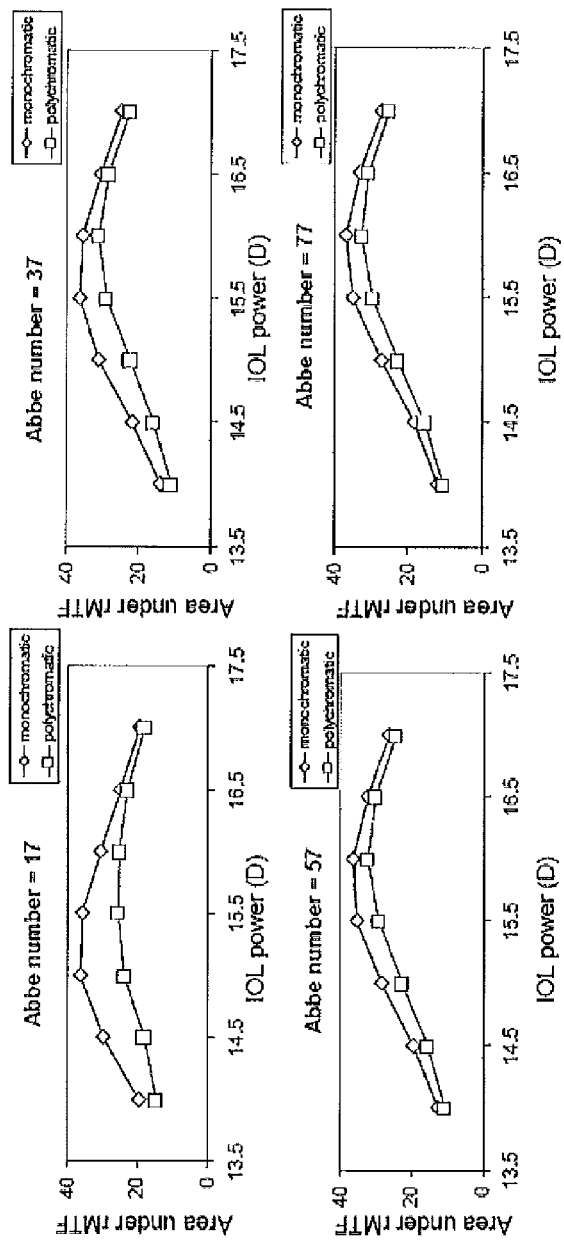
FIG. 9 shows the impact of the combined effect of monochromatic and chromatic aberrations on IOL power selection.

FIG. 9 shows the combined effect of considering monochromatic and chromatic aberrations in IOL power calculations. For one particular patient, the calculation is performed both monochromatically and polychromatically in the presence of his own optical aberrations for different IOL materials, leveled by different Abbe number. For higher dispersive materials the polychromatic calculation retrieves differences with respect to the monochromatic and therefore, the polychromatic ray tracing should be used in those particular cases. In other words, for materials with a lower Abbe number, it is more crucial to consider a polychromatic ray tracing, because there is a noticeable change in the IOL power predicted by the procedure with respect to the monochromatic calculation. However, for higher Abbe number, the polychromatic ray tracing is not as essential and a monochromatic treatment might speed up the process. Therefore, the ray tracing procedure may be performed only on one specific wavelength, which might be selected as that which maximizes the eye's spectral sensitivity either in photopic or mesopic conditions.

Figure 4B:
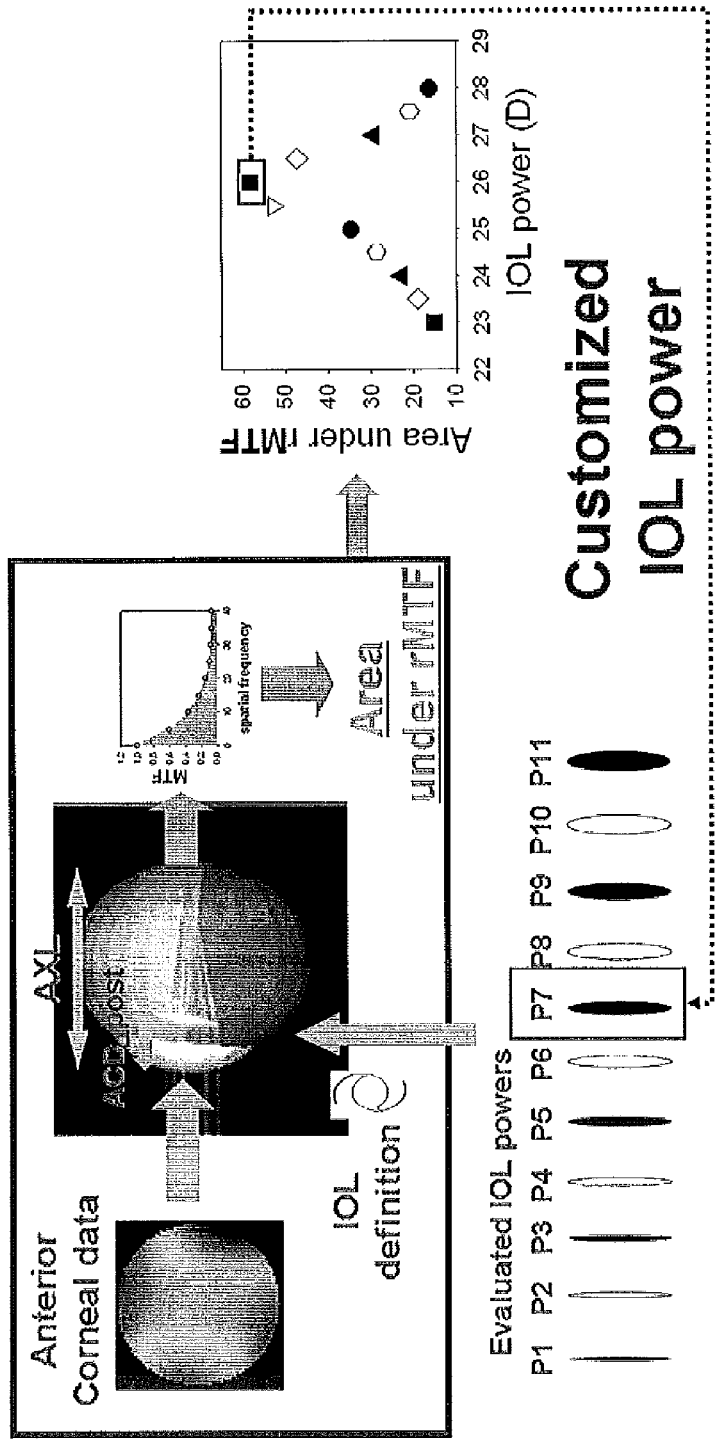

Those skilled in the art will appreciate that, for example, an optical design software simulation may be employed in order to provide such modeling, for example, using Zemax® software by Zemax Development Corporation of Bellevue, Wash. However, the ray tracing procedure can be fully programmed without the use of a specific design optical software. In the illustrative embodiment of FIG. 4A, a RpMTF at or at about 25 cpmm may be used, although the RpMTFs associated with another spatial frequency may alternatively be used. For example, a RpMTF at a different resolution, or the area under an RpMTF curve based on RPMTF values calculated at a plurality of resolutions, such as is shown in FIG. 4B, may be used. In this particular example, because there is no information related to the posterior cornea, the corneal equivalent refractive index may be selected automatically from the computer program between 1.330 and 1.324 depending on whether the patient is normal or has undergone prior LASIK surgery. The optimum IOL of the IOL models to be selected for implantation in the subject eye at step 350 is typically that which results in the highest RpMTF value for the RpMTF inquiry (i.e., RpMTF, area under the RpMTF, etc.) at step 340. For example, if RpMTF at 25 cpmm is used as an optical metric, the optimum IOL is that which results in the highest value of the RpMTF at that specific spatial frequency.

Figure 5:
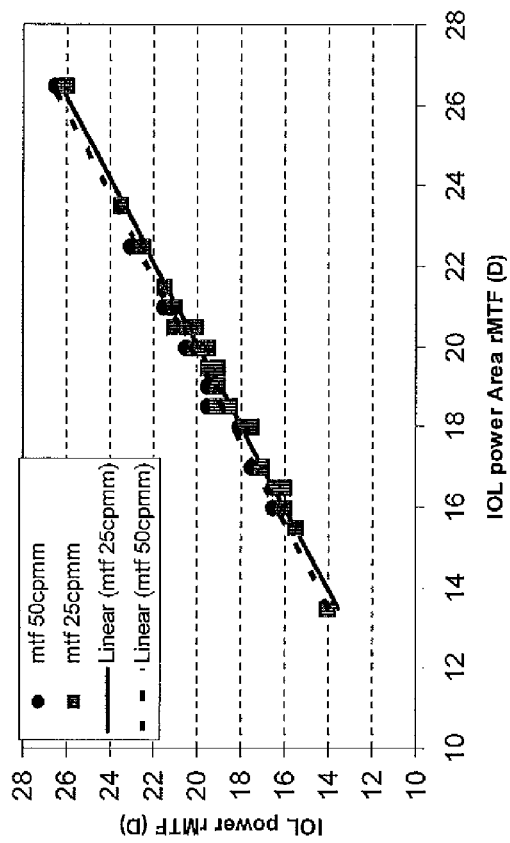
FIG. 5 shows a comparison of the results of the methods illustrated in FIGS. 4A and 4B.

However, although the area under the RpMTF curves may be more processing intensive, and thus may appreciably lengthen the calculation time, as compared to other RpMTF methods, such as the RpMTF point value calculation, the area under the RpMTF has not been found to significantly improve the resulting prediction of the optimal IOL at step 350. More particularly, FIG. 5 illustrates that the relationship between the IOL power retrieved by a single RpMTF point value (both at 25 or at 50 cpmm) and that calculated optimizing the area under an RpMTF curve defined by a plurality of such values is essentially linear.

Figure 6:
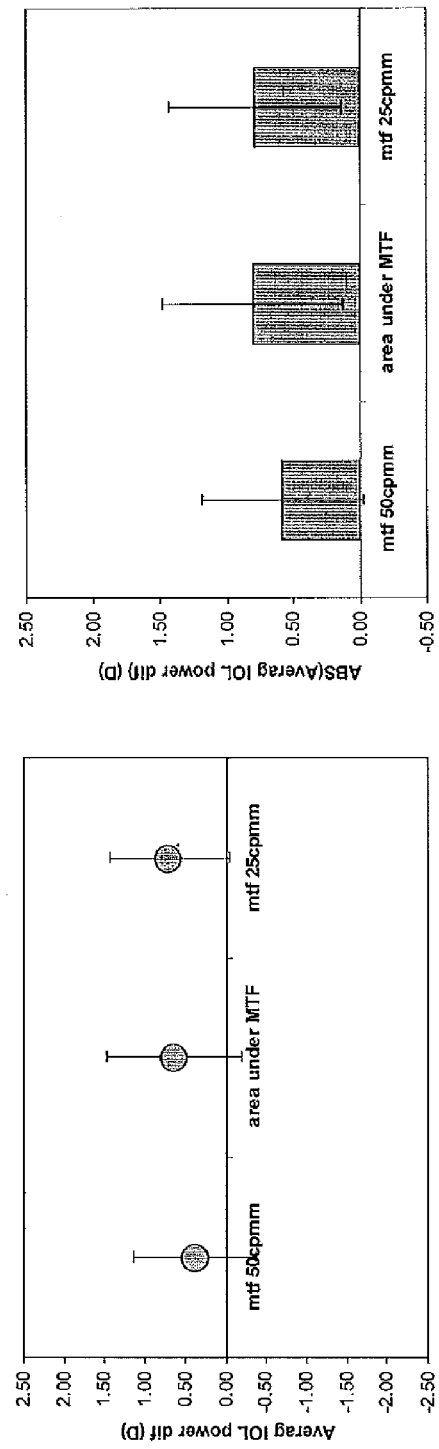
FIG. 6 is comparison between the IOL power predicted with different RpMTF metrics for 25 myopic postlasik patients.

Furthermore, a statistical analysis reveals that the IOL power selected by maximizing the RpMTF at 25 cpmm does not differ statistically from that retrieved by that calculated by maximizing the area under the RpMTF ($p>0.05$ for a two sample paired t-test), whereas the difference was statistically significant for the IOL power selected by the RpMTF at 50 cpmm ($p<0.05$). These results suggest that the same optimal IOL power is typically identified by method 299 whether a single RpMTF value is calculated at 25 cpmm for each IOL power, or the area under the RpMTF curve is optimized to calculate the IOL power FIG. 6 illustrates the difference between the optimum IOL power found after the surgery for 25 myopic post-Lasik patients and that calculated by different ray tracing procedures, with RpMTF at 50 cpmm, area under RpMTF and RpMTF at 25 cpmm as optimized parameters. As seen in FIG. 5, the accuracy achieved for the IOL power metric is similar. The residual error is hyperopic due to the fact that 1.330 was used as equivalent refractive index for these patients. This provides additional support that the equivalent refractive index should be changed for myopic post-Lasik patients.

Figure 7:
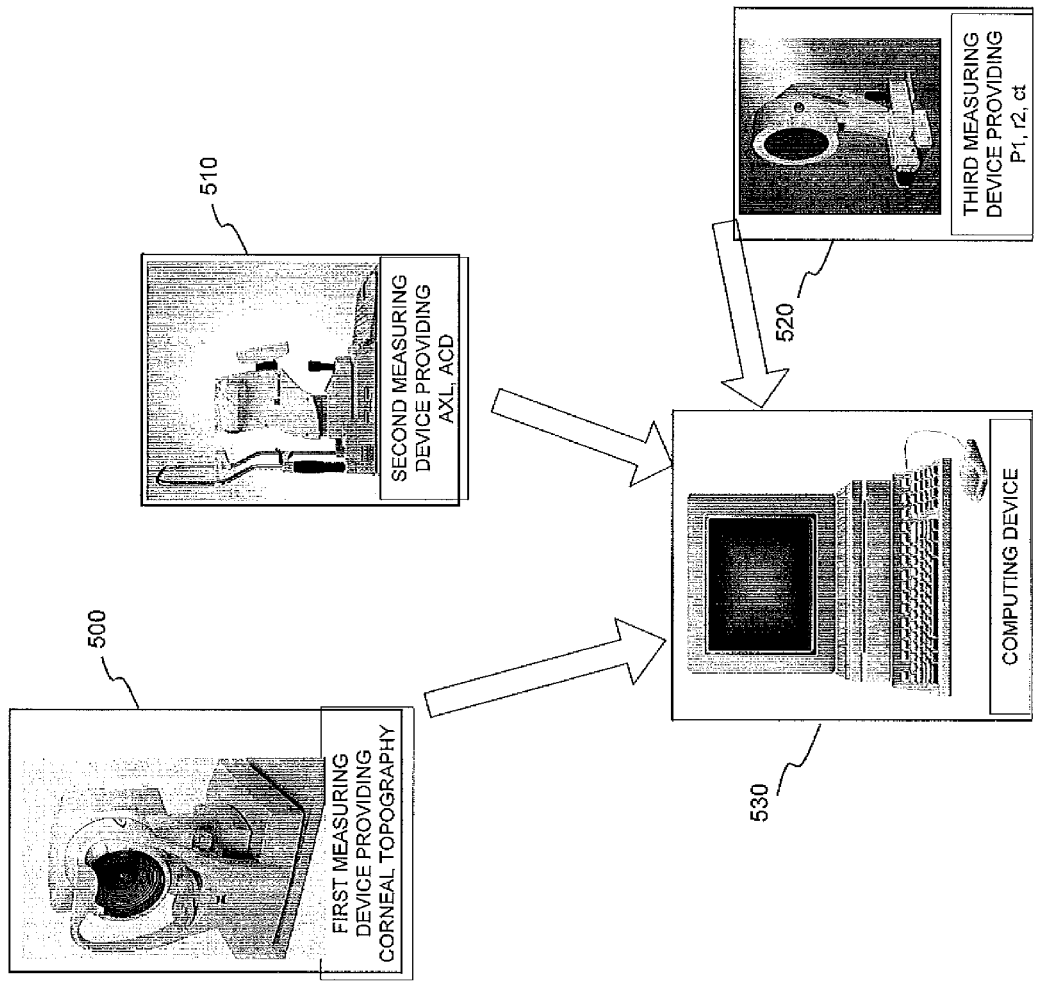
FIG. 7 is a block diagram of a system for selecting an IOL in accordance with the herein disclosed systems and methods.

FIG. 7 is a block diagram illustrating a system 499 for selecting an optimal IOL from a plurality of IOLs in accordance with the methods described above. The system comprises a first measuring device 500 that may provide information pertaining to the anterior corneal topography of a subject eye, and may be, for example, a Humphrey® ATLAS Corneal Topography System available from Carl Zeiss Meditec, Inc., or the like. The system also comprises a second measuring device 510 that may provide certain biometric dimensions of the subject eye, including the ACD and AXL, such as a Zeiss IOLMaster® or the like. In an embodiment, the system may also include a third measuring device 520, such as a Scheimpflug camera or posterior corneal topographer, as Pentacam from Oculus, which obtains data pertaining to the posterior corneal radius, and corneal thickness. Moreover, the third device might substitute the first herein described because it also provides measurements of the anterior cornea. The first and second, and optionally the third, measuring devices may provide data that may be input into computing device 530, for example, via a manual or an automated interface. Computing device 530 may perform the modeling and calculations described hereinabove with respect to method 299, and may output an optimal IOL from among a plurality of IOLs, such as from among a series of IOLs of an IOL model. The optimal IOL is the one that is most likely to provide the desired characteristics upon for implantation in the subject eye. In exemplary embodiments, any two or more of the elements of system 499 may be incorporated into a single device, or comprised within a single housing.

In addition to monofocal IOLs, multifocal (diffractive or refractive) or toric IOLS, are also covered by the embodiments disclosed herein.

If a toric IOL is not used to correct corneal astigmatism, the astigmatism may be addressed with a spherical IOL using the herein disclosed systems and methods. For example, the IOL power calculated may minimize distortion due to an astigmatic cornea by calculating the IOL power that achieves the circle of least confusion of the system composed by the eye and IOL. This may be done by correcting corneal astigmatism from anterior corneal topography. Optimizing such an optical system in accordance with the herein disclosed systems and methods may be particularly advantageous in patients with low amounts of corneal astigmatism, for whom visual performance is still good without the need of a toric IOL.

Of note, in the absence of measured data pertaining to the posterior corneal surface and/or corneal thickness, such as in the event of non-inclusion of third measuring device 520 in the system of the present invention, an equivalent refractive index of 1.330 may be selected for normal eyes in the eye model of the herein described systems and methods. It may be appreciated by one of skill in the art that, on average using prior art models, the resulting residual refraction is slightly hyperopic for prior myopic post-Lasik patients, as indicated in FIG. 6. Accordingly, the equivalent refractive index may preferably be adjusted accordingly in the herein disclosed systems and methods.

In contrast, an equivalent refractive index of 1.324 may be selected for postlasik eyes in the eye model of the herein described systems and methods, if posterior corneal data are not available. For example, IOL power was calculated for cataract patients, who had undergone Lasik surgery to correct myopia, using the herein described method 299 and system 499, with the optimization being for the RpMTF at 25 cpmm, and using both average and personalized equivalent refractive index. Then, for each patient, a ray tracing IOL power prediction was retrieved considering 1.330 (equivalent refractive index for normals), 1.324 (resulting as the average through which all the customized equivalent refractive index is calculated) and those retrieved from individual data, considering a customized equivalent refractive index for each patient.

Because of the absence of posterior corneal data, the procedure to obtain customized equivalent refractive index was adjusted to consider r2 (posterior corneal radius) as that calculated from the anterior pre-Lasik corneal radius (r1) multiplied by the constant ratio 0.838 that is found in the literature (Dubbelman M, Sicam V A, Van der Heijde G L, "The shape of the anterior and posterior surface of the aging human cornea", Vision Res. 2006; 46: 993-1001) between the posterior and anterior radius in normal patients, which is the case for these patients before undergoing LASIK surgery. From that, the procedure described to calculate customized equivalent refractive index hereinbefore described was applied and an equivalent refractive index was calculated for each patient, with the following results:

average neff from preoperative data→1.324±0.003
personalized neff from preoperative data→ranging from 1.316 to 1.329.

Figure 8:
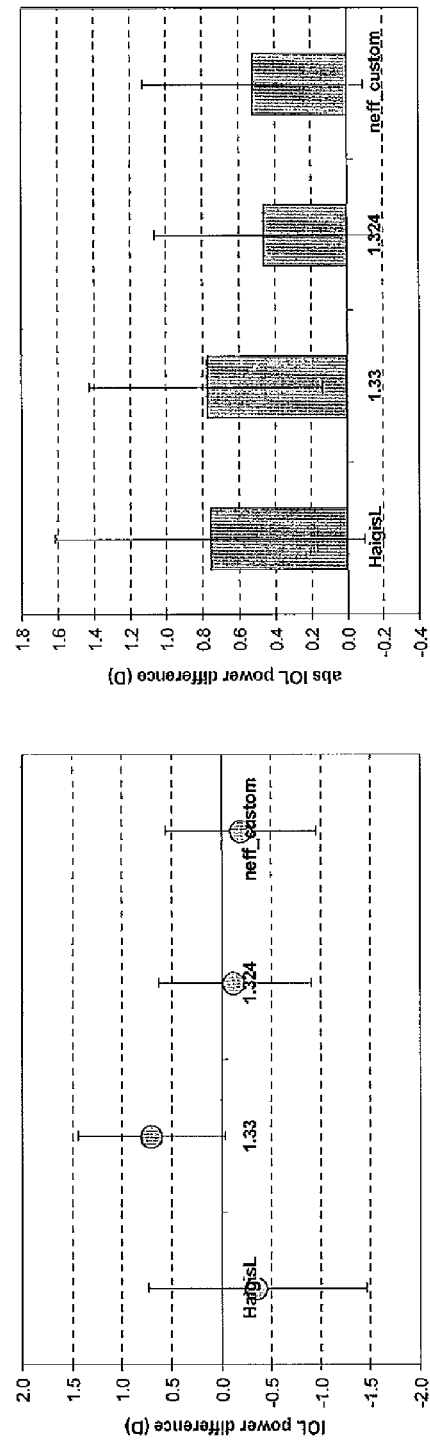
FIG. 8 shows differences with respect the optimum IOL power when different equivalent refractive index are considered for myopic post-Lasik patients, as well as the for the current state of art.

IOL power difference with respect the optimum IOL power retrieved after the surgery was calculated for all of these methods, and for the Haigis L regression. The Haigis L is typically considered as representative of the current state of art for IOL power calculations in postlasik eyes. These data are plotted in FIG. 8. In view of these data, it may be appreciated by one of skill in the art that 1.324 is a desirable equivalent refractive index to use in the herein described systems and methods for postlasik eyes.

This equivalent refractive index might be personally optimized, following the procedure above described to calculate it, from data of multiple patients in the same pre-cataract conditions. Therefore, the equivalent refractive index might be personalized for normals, myopic or hyperopic post-LASIK.

Those of ordinary skill in the art may recognize that many modifications and variations of the herein disclosed systems and methods may be implemented without departing from the spirit or scope of the invention. Thus, it is intended that the present invention covers such modifications and variations provided they come within the scope the appended claims and their equivalents.

What is claimed is:

1. A method of selecting an intraocular lens to be implanted in a subject eye, comprising:
   measuring a corneal topography, an axial length, and an anterior chamber depth of a subject eye; and
   for each of a plurality of intraocular lenses:
      modeling the subject eye with one of the plurality of intraocular lenses in accordance with said measuring;
      performing a ray tracing using said eye model;
      calculating from said ray tracing a RpMTF or RMTF; and
      selecting one of the plurality of intraocular lenses corresponding to a highest one of the RpMTF or RMTF value for implanting in the subject eye, wherein RpMTF is the radially averaged polychromatic modulation transfer function and RMTF is the radially averaged monochromatic transfer function.

2. The method of claim 1, wherein the step of modeling the eye further comprises a prediction of a position of the IOL when implanted in the subject eye.

3. The method of claim 2, wherein the prediction is based on a regression analysis of historical data relating preoperative anterior chamber depth (ACD) to postoperative ones of the ACD.

4. The method of claim 1, wherein the calculating of the ray tracing is performed at least at six wavelengths, if a polychromatic ray tracing is used, or at a unique wavelength for monochromatic ray tracing.

5. The method of claim 1, wherein the ray tracing is performed at a 4 mm entrance pupil.

6. The method of claim 1, wherein the RpMTF or RMTF value is at a spatial frequency of 25 cpmm.

7. The method of claim 1, wherein said calculating from the ray tracing of the RpMTF or RMTF value comprises calculating the area under a plurality of RpMTF or RMTF values defined for different spatial frequencies.

8. The method of claim 1, wherein the modeling further comprises an equivalent refractive index accounting for refraction due to the posterior cornea of the subject eye.

9. The method of claim 8, wherein the equivalent refractive index is 1.324 if the subject eye has previously undergone Lasik surgery for myopia, and 1.330 if the subject eye has not previously undergone any Lasik surgery.

10. The method of claim 9, where the equivalent refractive index for different types of population are personalized.

11. The method of claim 8, wherein the equivalent refractive index is based at least on measurements of a posterior corneal radius and a corneal thickness.

12. The method of claim 1, wherein the modeling further comprises a representation of the posterior cornea.

13. A system for identifying an intraocular lens (IOL) for implantation, comprising:
   a first measuring device capable of providing a plurality of characteristics of a subject eye;
   a computing device programmed, for an IOL, to:
      predict a position of one of the IOLs when implanted in the subject eye, based on the plurality of characteristics;
      modeling the subject eye based on the plurality of characteristics and the predicted IOL position;
      perform a ray tracing based on said eye model;
      calculate from said ray tracing a RpMTF or RMTF value; and
      compare a plurality of RpMTF or RMTF values corresponding to the plurality of IOLs to identify a highest one of the RpMTF or RMTF values;
      identify one IOL from the plurality of IOLs corresponding to the highest one of the RpMTF or RMTF values; and
      output the identified one IOL.

14. The system of claim 13, wherein the eye model includes an equivalent refractive index accounting for refraction due to the posterior cornea.

15. The system of claim 14, wherein the equivalent refractive index is 1.324 if the subject eye has previously undergone an Lasik for myopia, and is 1.330 if the subject eye has not previously undergone any Lasik surgery.

16. The system of claim 13, further comprising a second measuring device capable of providing a measured a posterior corneal radius (r2), and a corneal thickness (ct),
   wherein the equivalent refractive index incorporates the provided r2 and ct.

17. The system of claim 13, further comprising a second measuring device capable of providing a representation of the posterior corneal surface.

18. A tangible computer-readable storage device storing computer instructions which, when read by a computer, cause the computer to perform a method comprising:
receiving a plurality of eye characteristics of a subject eye;
for each of a plurality of intraocular lenses (IOLs):
simulating a geometry of the subject eye with each of the plurality of intraocular lenses (IOL) implanted, in accordance with the plurality of eye characteristics;
calculating a ray tracing of said simulating; and
calculating from said ray tracing a RpMTF or RMTF value; and
selecting one of the plurality of IOLs corresponding to a highest one of the RpMTF or RMTF values for implanting in the subject eye, wherein RpMTF is the radially averaged polychromatic modulation transfer function and RMTF is the radially averaged monochromatic transfer function.

19. The tangible computer-readable storage device of claim 18, wherein the performed method further comprises outputting the identity of the selected IOL.

20. The tangible computer-readable storage device of claim 18, wherein the calculating of the RpMTF or RMTF value is a point value at a frequency of 25 cpmm.

21. The tangible computer-readable storage device of claim 18, wherein said calculating from the ray tracing of the RpMTF or RMTF value comprises calculating the area under a plurality of RpMTF or RMTF curves.

\* \* \* \* \*